United States Patent [19]
Ellison

[11] Patent Number: 5,318,017
[45] Date of Patent: Jun. 7, 1994

[54] GUIDE FOR TRANSESOPHAGEAL ECHO PROBE

[76] Inventor: Lee H. Ellison, 80 Soby Dr., West Hartford, Conn. 06107

[21] Appl. No.: 972,255

[22] Filed: Nov. 5, 1992

[51] Int. Cl.⁵ ............................................. A61B 10/00
[52] U.S. Cl. ........................... 128/200.24; 128/660.01; 128/662.06; 128/695; 128/657; 128/658
[58] Field of Search ...................... 128/200.24, 200.26, 128/207.14, 660.01, 662.06, 695, 656, 657, 658, 10, DIG. 26; 604/270

[56] References Cited

U.S. PATENT DOCUMENTS

| | | | |
|---|---|---|---|
| 2,693,182 | 11/1954 | Phillips | 128/200.26 |
| 3,499,435 | 3/1970 | Rockwell et al. | 128/671 |
| 3,756,244 | 9/1973 | Kinnear et al. | 128/207.14 |
| 4,068,658 | 1/1978 | Berman . | |
| 4,090,518 | 5/1978 | Elam | 128/207.15 |
| 4,166,467 | 9/1979 | Abramson | 128/207.14 |
| 4,167,946 | 9/1979 | Sandstrom | 128/207.17 |
| 4,304,240 | 12/1981 | Perlin | 128/671 |
| 4,316,391 | 2/1982 | Tickner | 128/660.01 X |
| 4,351,330 | 9/1982 | Scarberry | 128/207.15 |
| 4,363,320 | 12/1982 | Kossove | 128/207.14 |
| 4,475,555 | 10/1984 | Linder | 128/670 |
| 4,495,945 | 1/1985 | Liegner | 128/200.26 |
| 4,529,400 | 7/1985 | Scholten | 604/95 |
| 4,778,455 | 10/1988 | Kousai | 604/270 |
| 4,850,983 | 7/1989 | Brenneman | 604/270 |
| 5,020,534 | 6/1991 | Pell et al. | 128/207.15 |
| 5,024,218 | 6/1991 | Ovassapian | 128/200.26 |
| 5,038,766 | 8/1991 | Parker | 182/200.26 |
| 5,050,610 | 9/1991 | Oaks et al. | 128/662.06 |

FOREIGN PATENT DOCUMENTS

| | | | |
|---|---|---|---|
| 61332 | 9/1982 | European Pat. Off. | 128/662.06 |
| 94791 | 11/1983 | European Pat. Off. | 128/662.06 |

*Primary Examiner*—Edgar S. Burr
*Assistant Examiner*—Eric P. Raciti

[57] ABSTRACT

A guide for an esophageal echo probe includes a bite block with a collar about one end thereof to seat about the patient's mouth and a sleeve of low friction, flexible, form-retaining material having a generally arcuate configuration and dimensioned and configured to extend from the patient's mouth through the ovopharynx and into the esophagus. A secondary guide extends along the length of the bite block and sleeve and provides a passage seating an orogastric tube to lead the sleeve through the ovopharynx and into the esophagus. The passage through the bite block and sleeve is dimensioned to slidably receive and guide a transesophageal echo probe for placement in the patient's body.

18 Claims, 2 Drawing Sheets

GUIDE FOR TRANSESOPHAGEAL ECHO PROBE

BACKGROUND OF THE INVENTION

The present invention relates to guides for medical instrumentation, and, more particularly, to a guide for a transesophageal echo probe.

Recent developments in heart surgery for repaired diseased arteroventricular valves and replacement of diseased semilunar valves have resulted in increasing usage of homograft valves, i.e., valves from organ donors, instead of the synthetic valves which have heretofore been most widely used. Whether a valve is repaired or a homograft valve or synthetic valve is utilized, the surgeon wishes to ensure that the operation of the valve is satisfactory while the patient is still coupled to the bypass machine and before completely closing the thoracic cavity.

To provide such an evaluation of valve operation, or even evaluate cardiac function after any operation, an esophageal echo probe is introduced through the mouth and passed downwardly into the esophagus to a point within the patient's body where the operation of the valve can be monitored. The probe has a diameter of approximately ⅞ inch and requires guidance into the esophagus. Despite the patient's unconscious state, there is a substantial gag effect and there is also a tendency for the patient to bite down on anything which is being introduced into the mouth and being forced downwardly. Echo probes are expensive instruments having a value on the order of $30,000, and they are extremely sensitive; thus a patient who bit the instrument could cause substantial damage.

Furthermore, the size of the probe is such that there is frictional contact between its surface and the tissue about the passages through the pharynx and esophagus, and this can result in damage to the tissue.

Accordingly, it is an object of the present invention to provide a novel guide which, when placed in the patient, will facilitate insertion and guidance of the transesophageal echo probe into the desired position within the patient's body.

It is also an object to provide such a guide which will protect the probe from injury by the patient's teeth.

Another object is to provide such a guide which will minimize the gag effect on the patient resulting from the insertion of a device of such size.

A further object is to provide a novel method for inserting a transesophageal echo probe into a patient utilizing a guide which will facilitate its introduction without damage to the pharynx and esophagus.

SUMMARY OF THE INVENTION

It has now been found that the foregoing and related objects may be readily attained in a guide for an esophageal echo probe which includes a bite block of relatively bite resistant material and providing a passage therethrough. The bite block has a collar about one end thereof to seat about the patient's mouth and a body dimensioned and configured to seat within the patient's mouth.

A sleeve of low friction, flexible form-retaining material extends from the other end of the bite block and is of generally arcuate configuration. The sleeve is dimensioned and configured to extend from the bite block in the patient's mouth through the ovopharynx and into the esophagus. Also included is secondary guide means extending the length of the bite block and sleeve, and providing a passage dimensioned to slidably seat an orogastric tube to lead the sleeve through the ovopharynx and into the esophagus. The passage through the bite block and the sleeve is dimensioned to slidably receive and guide a transesophageal echo probe for placement in the patient's body.

Generally, the bite block is fabricated from synthetic resin and is relatively rigid, and the sleeve is also fabricated from synthetic resin. The sleeve extends about the body of the bite block and desirably there is included a resiliently deformable synthetic resin layer between the sleeve and body of the bite block.

Preferably, the sleeve tapers to a reduced cross section at its end spaced from the bite block, and the secondary guide means is provided along the outer surface of the sleeve. The collar of the bite block has a passage therethrough communicating with the passage of the secondary guide means. Conveniently, the secondary guide means is provided by a flexible synthetic resin strip having its side margins bonded to the sleeve.

In the method for inserting the transesophageal echo probe into a patient, the esophageal guide is inserted into the mouth of the patient and guided into the esophagus. The guide is manipulated to cause the sleeve to slide along the orogastric tube and pass through the patient's ovopharynx and into the esophagus until the bite block seats in the patient's mouth. Finally, the esophageal echo probe is slid through the passage of the bite block passage and the passage in the tube to the desired position in the patient's body.

DETAILED DESCRIPTION OF THE PREFERRED EMBODIMENT

Figure 1:
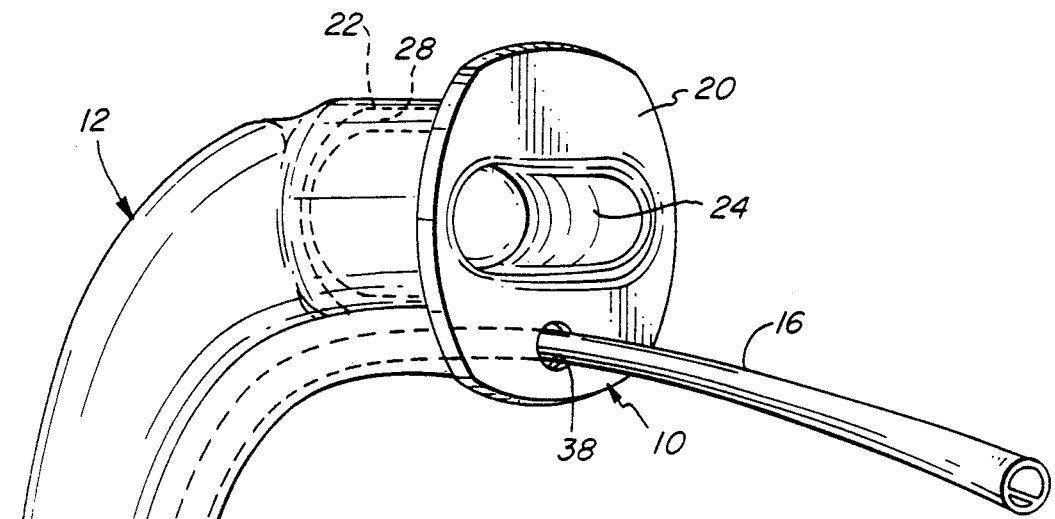
FIG. 1 is a fragmentary perspective view of a guide for a transesophageal echo probe embodying the present invention with the orogastric tube fragmentarily illustrated.
Figure 2:
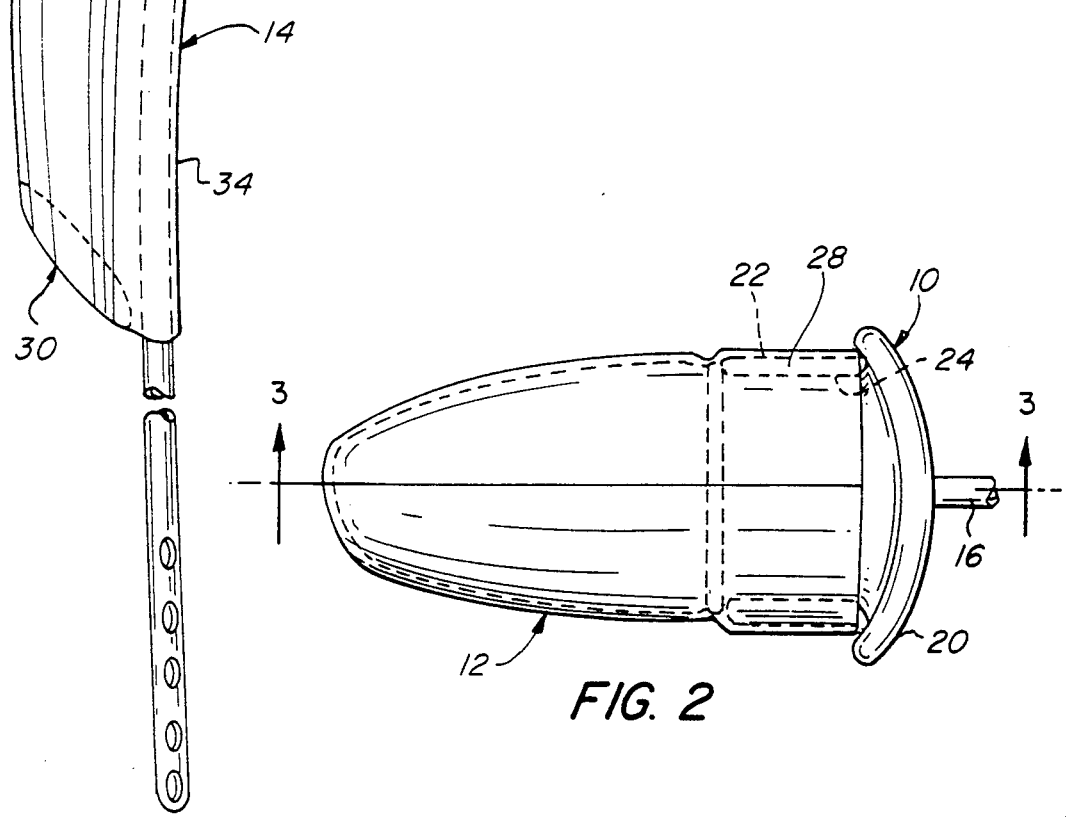
FIG. 2 is a fragmentary elevational view thereof.
Figure 3:
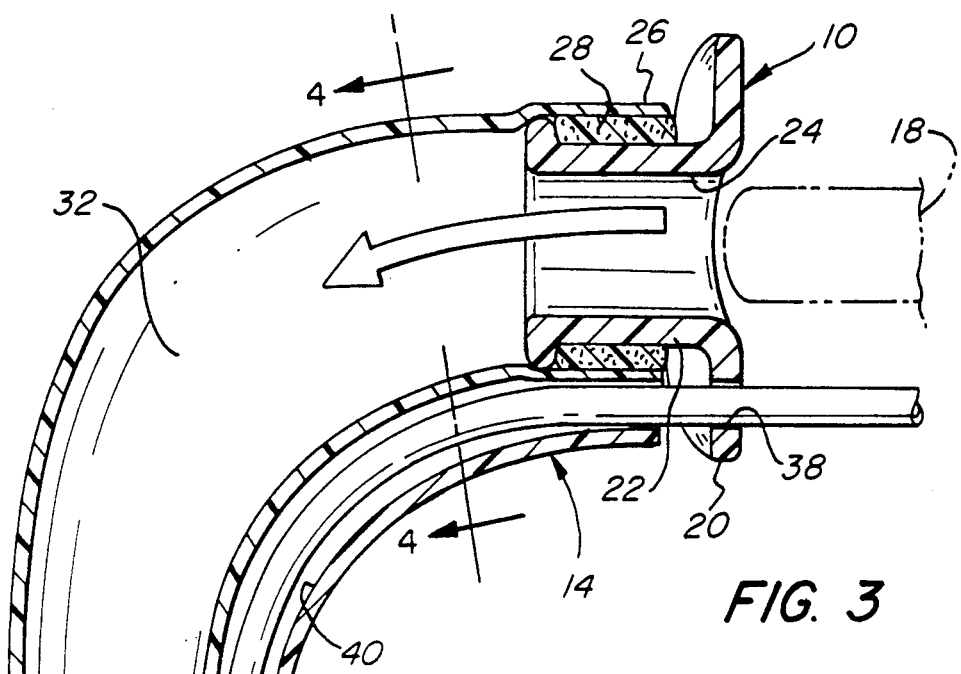
FIG. 3 is a sectional view along the line 3—3 of FIG. 2 with a transesophageal echo probe fragmentarily shown in phantom line as it is about to be introduced into the guide.
Figure 4:
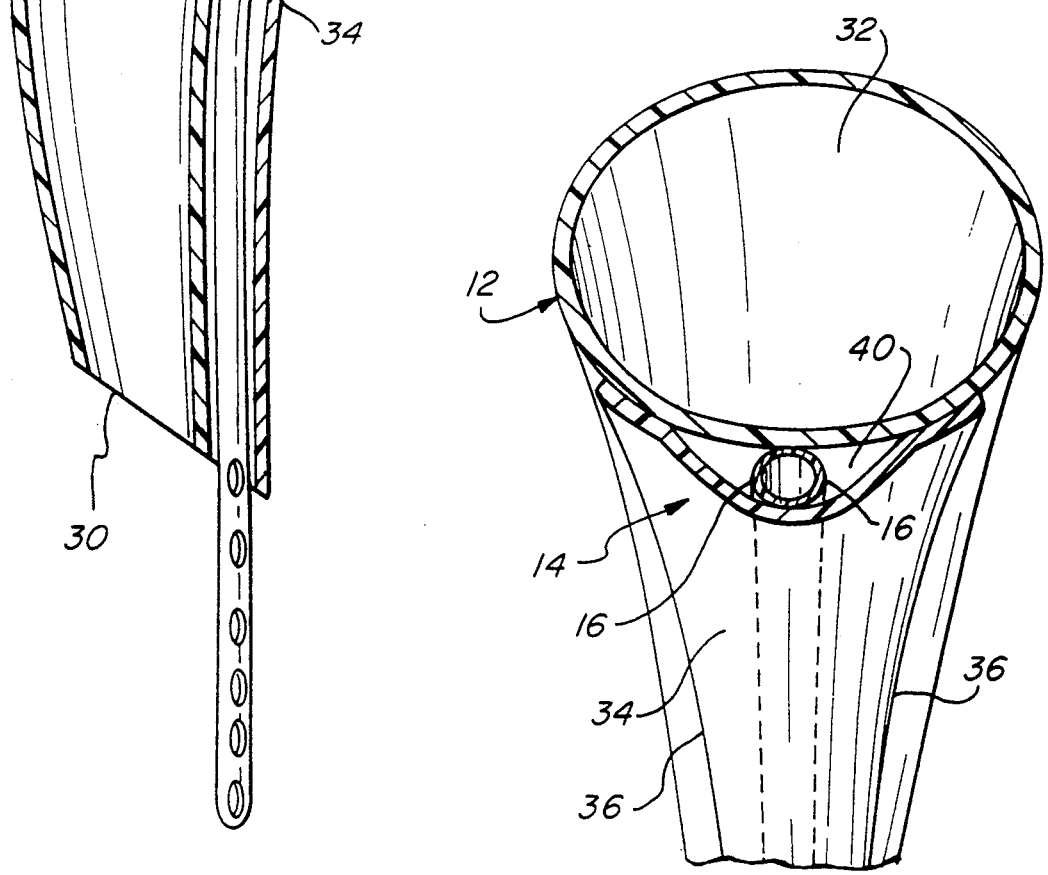
FIG. 4 is a sectional view along the line 4—4 of FIG. 3.

Turning now to the accompanying drawings in detail, a guide embodying the present invention is comprised of a bite block generally designated by the numeral 10, a flexible sleeve which extends therefrom and which is generally designated by the numeral 12, and a secondary guide generally designated by the numeral 14 extending along the length of the bite block 10 and sleeve 12. As seen in FIG. 3, a transesophageal echo probe 18 is fragmentarily illustrated in phantom line as it is about to be introduced into the guide, and the orogastric probe 16 is illustrated as assembled with the secondary guide 14 to facilitate the placement of the guide in the proper position.

Turning first in detail to the bite block 10, it is integrally molded or fabricated from a relatively rigid and bite resistant synthetic resin with a collar 20 extending about one end thereof and a body 22, and with a passage 24 which extends therethrough. In use, the bite block 10 is introduced into the patient's mouth and the collar 20 will abut the patient's face about the mouth.

The sleeve 12 is fabricated from a form retaining, flexible synthetic resin of relatively low frictional characteristics so that it will flex and move fairly easily through the patient's mouth and ovopharynx and into the patient's esophagus. The sleeve 12 is fabricated with a generally arcuate configuration to conform to the path which it will assume. As seen, the upper end portion 26 of the sleeve 12 extends about the periphery of the body 22 of the bite block 10, and a layer of resiliently deformable synthetic resin 28 is provided therebetween. The layer 28, sleeve 12 and bite block 10 are adhesively bonded to secure the components in assembly. As also seen, the sleeve 12 tapers in cross section so that the lower end portion 30 thereof is of reduced dimension, and the tubular nature of the sleeve 12 provides a passage 32 extending therethrough.

Secured to the outer surface of the sleeve 12 is an elongated strip 34 of flexible synthetic resin which is adhesively bonded along its side margins 36 to provide a relatively small channel 40 between the strip 34 and the sleeve 12, thus forming the secondary guide 14 through which the orogastric tube 16 extends. The collar 20 of the bite block 10 has an aperture 38 extending therethrough in alignment with the channel 40 to provide a passage for the orogastric tube 16.

In using the guide of the present invention, the orogastric tube 16 may be initially introduced into the mouth of the patient and pushed downwardly into the patient's esophagus before the guide is assembled thereto. After the orogastric tube has been fully seated, the guide is slid onto the orogastric tube 16 which is received within the channel 40. The sleeve 12 of the guide is introduced into the patient's mouth, and the guide is manipulated to cause the end 30 to enter the throat. During this movement, the orogastric tube 16 facilitates and guides the movement of the sleeve 12. The form-retaining characteristics of the sleeve 12 allow it to flex while providing the requisite stiffness to enable it to be pushed downwardly past the ovopharynx and into the esophagus. This movement is continued until the bite block 10 seats in the patient's mouth with the collar 20 abutting the patient's face about the mouth.

At this point, the guide is fully seated and the transesophageal echo probe 18 may be inserted into the passage 24 as shown in FIG. 3. The probe 18 will be guided in the passage 24 into the esophagus and the surgeon can place it in the desired position to monitor valve action.

After the surgeon has tested the functioning of the valves in the patient, the probe 18 is removed and then the guide of the present invention is removed from the patient.

As will be appreciated, the guide of the present invention at all times protects the probe 18 from possible injury by the patient's teeth and it provides a relatively low friction surface for movement of the probe 18 therethrough.

various resins may be utilized for fabrication of the bite block including polyolefins such as polyethylene and polypropylene and interpolymers thereof, polyamide, polytetrafluoroethylene and silicones.

To provide the sleeve (and secondary guide means) with the desired low friction characteristics and also provide a material which is substantially inert, resins such as polytetraflorolethylene and silicones are preferred. The durometer or flexibility of the resin should be selected to provide sufficient stiffness to allow the sleeve to retain its basic structural configuration as it is manipulated and advanced into the patient's ovopharynx and esophagus. For convenience in effecting bonding, the strip providing the secondary guide passage is conveniently fabricated from the same resin. The fabrication of the tube and secondary guide may be effected by an extrusion die or a mold to produce the two components as an integral element. If extruded, the tapering and arching may be effected by stretching and molding and forming the material as it is being extruded. For convenience, it has been found that a strip of sheet material may be utilized to form the tapered structure and circular cross section of the sleeve. Thereafter a second strip of material may be bonded thereto to provide the secondary guide passage. Bonding of the material of the sleeve to itself and of the secondary guide to the sleeve may be effected by separately applied adhesive, sonic welding or any other suitable bonding procedure.

The layer of resiliently deformable material between the bite block and the sleeve is conveniently provided by a flexible foam fabricated from resins such as polyurethane and polyolefins. This layer of resin, the bite block and tube may all be secured together by separately applied adhesive, ultrasonic bonding or any other suitable technique.

As a specific example of the dimensioning of a suitable guide, a bite block is formed of polypropylene with a body circumference of 10 cm. A sleeve is fabricated from a strip of polytetrafluoroethylene sheeting, and its overlapping edges are bonded. A second strip of such sheeting is bonded thereto to provide the secondary guide passage. The length of sleeve is 20 cm which is sufficient to ensure that its inner end will extend into the esophagus of most adults.

Thus, it can be seen from the foregoing description and attached drawings that the novel guide of the present invention may be readily fabricated to facilitate insertion of a transesophageal echo probe into a proper position within the patient's body. It will protect the probe from injury by the patient's teeth and it will minimize the gag effect and irritation of the patient's tissues.

I claim:
1. A guide for an esophageal probe comprising:
(a) a bite block of relatively bite resistant material and providing a passage therethrough, said bite block having a first end and a second end, said first end having a collar including means for seating about a patient's mouth, said bite block further having a body dimensioned and configured to seat within a patient's mouth;
(b) a hollow sleeve of low friction, relatively flexible, form-retaining material extending from said second end of said bite block, said hollow sleeve having a generally arcuate configuration and being dimensioned and configured to extend from a patient's mouth through the oropharynx and into the esophagus, and having an interior portion in communication with said passage of said bite block; and
(c) secondary guide means for slidably seating an orogastric tube extending the length of said bite block and said hollow sleeve for guiding along an orogastric tube through the oropharynx into the esophagus, said passage of said bite block and said hollow sleeve being dimensioned to slidably receive therethrough and guide a transesophageal probe for placement in a patient's body.

2. The esophageal probe guide in accordance with claim 1 wherein said bite block is fabricated from synthetic resin and is relatively rigid.

3. The esophageal probe guide in accordance with claim 1 wherein said sleeve is fabricated from synthetic resin.

4. The esophageal probe guide in accordance with claim 1 wherein said sleeve extends about said body of said bite block.

5. The esophageal guide in accordance with claim 4 wherein there is included a resiliently deformable synthetic resin layer between said sleeve and body.

6. The esophageal probe guide in accordance with claim 1 wherein said sleeve tapers to a reduced cross section at its end spaced from said bite block.

7. The esophageal probe guide in accordance with claim 1 wherein said secondary guide means is provided along the outer surface of said body of said bite block and of said sleeve.

8. The esophageal probe guide in accordance with claim 7 wherein said collar of said bite block has a passage therethrough communicating with said passage of said secondary guide means.

9. The esophageal probe guide in accordance with claim 7 wherein said secondary guide means is provided by a flexible synthetic resin strip having end and side margins, said side margins being bonded to said sleeve.

10. A guide for an esophageal probe comprising:
(a) a bite block of relatively bite resistant material and providing a passage therethrough, said bite block having a first end and a second end, said first end having a collar including means for seating about a patient's mouth, said bite block further having a body dimensioned and configured to seat within a patient's mouth;
(b) a hollow sleeve of low friction, relatively flexible, form-retaining material extending from said second end of said bite block, said hollow sleeve having a generally arcuate configuration and being dimensioned and configured to extend from a patient's mouth through the oropharynx and into the esophagus, and having an interior portion in communication with said passage of said bite block, and said sleeve being fabricated from a synthetic resin and extending about said body of said bite block; and
(c) secondary guide means for slidably seating an orogastric tube extending the length of said bite block and sleeve, said guide means being provided along the outer surface of said body of said bite block and sleeve and providing a passage dimensioned to slidably seat an orogastric tube to lead said sleeve through the oropharynx into the esophagus, said passage of said bite block and said hollow sleeve being dimensioned to slidably receive therethrough and guide a transesophageal probe for placement in a patient's body.

11. The esophageal probe guide in accordance with claim 10 wherein said bite block is fabricated from a relatively rigid synthetic resin and said sleeve tapers to a reduced cross section at its end spaced from said bite block.

12. The esophageal probe guide in accordance with claim 10 wherein there is included a layer of resiliently deformable material between said sleeve and body.

13. The esophageal probe guide in accordance with claim 10 wherein said collar of said bite block has a passage therethrough communicating with said passage of said secondary guide means and said secondary guide means is provided by a flexible synthetic resin strip having end and side margins, said side margins being bonded to said sleeve.

14. In a method for inserting a transesophageal probe into a patient, the steps comprising:
(a) providing a guide comprising:
(i) a bite block of relatively bite resistant material and providing a passage therethrough, said bite block having a first end and a second end, said first end having a collar including means for seating about a patient's mouth, said bite block further having a body dimensioned and configured to seat within a patient's mouth;
(ii) a hollow sleeve of low friction, relatively flexible, form-retaining material extending from said second end of said bite block, said hollow sleeve having a generally arcuate configuration and being dimensioned and configured to extend from a patient's mouth through the oropharynx and into the esophagus, and having an interior portion in communication with said passage of side bite block; and
(iii) secondary guide means for slidably seating an orogastric tube extending the length of said bite block and hollow sleeve for guiding along an orogastric tube through the ovopharynx into the esophagus, said passage in said bite block and said hollow sleeve being dimensioned to slidably receive and guide a transesophageal probe for placement in a patient's body;
(b) inserting into the mouth of a patient an orogastric tube and said guide, said tube extending along said secondary guide means;
(c) manipulating said guide to cause said sleeve to slide along said orogastric tube and pass through the patient's oropharynx and into the esophagus and said bite block to seat in the patient's mouth; and
(d) sliding an esophageal echo probe through said passage of said bite block and said tube into the patient's body.

15. The method in accordance with claim 14 wherein said step of providing a guide further comprises the step of providing a guide in which said bite block is fabricated from a relatively rigid synthetic resin, said sleeve is fabricated from a synthetic resin, said sleeve is fabricated from a synthetic resin, and said sleeve extends about said body of said bite block.

16. The method in accordance with claim 14 wherein said step of providing a guide further comprises the step of providing a guide in which there is included a layer of resiliently deformable plastic material between said sleeve and body, and wherein said sleeve tapers to a reduced cross section at its end spaced from said bite block.

17. The method in accordance with claim 14 wherein said step of providing a guide further comprises the step of providing a guide in which said secondary guide means is provided along the outer surface of said body of said bite block and sleeve.

18. The method in accordance with claim 17 wherein said step of providing a guide further comprises the step of providing a guide in which said collar of said bite block has a passage therethrough communicating with said passage of said secondary guide means, and wherein said secondary guide means is provided by a flexible synthetic resin strip having its side margins bonded to said sleeve.

* * * * *